United States Patent [19]

Prince

[11] Patent Number: 5,417,213

[45] Date of Patent: May 23, 1995

[54] MAGNETIC RESONANCE ARTERIOGRAPHY WITH DYNAMIC INTRAVENOUS CONTRAST AGENTS

[76] Inventor: Martin R. Prince, 202 Delafield St., Ann Arbor, Mich. 48105

[21] Appl. No.: 71,970

[22] Filed: Jun. 7, 1993

[51] Int. Cl.$^6$ ............................................. A61B 5/055
[52] U.S. Cl. ............................. 128/653.3; 128/653.4; 128/654; 128/655; 424/9.3; 424/9.36
[58] Field of Search .................. 128/653.3, 653.4, 654, 128/659, 655; 424/9

[56] References Cited

U.S. PATENT DOCUMENTS

| | | | |
|---|---|---|---|
| 3,973,554 | 8/1976 | Tipton | 128/654 X |
| 4,006,736 | 2/1977 | Kranys et al. | 128/655 |
| 4,585,008 | 4/1986 | Jarkewicz | 128/654 |
| 4,585,941 | 4/1986 | Bergner | 128/654 X |
| 4,718,424 | 1/1988 | Nishimura . | |
| 4,770,183 | 9/1988 | Groman et al. . | |
| 4,777,957 | 10/1988 | Wehroli et al. | 128/653.3 |
| 4,822,594 | 4/1989 | Gibby . | |
| 4,826,673 | 5/1989 | Dean et al. . | |
| 4,865,043 | 9/1989 | Shimoni | 128/654 X |
| 4,877,599 | 10/1989 | Lees . | |
| 4,880,008 | 11/1989 | Lauffer | 128/653.4 |

(List continued on next page.)

OTHER PUBLICATIONS

"Cerebrovascular Magnetic Resonance Angiography", Wesbey et al., J. Vascular Sugery 1992, vol. 16, No. 4, pp. 619–632.
"Volume MR Angiography: Methods to Achieve Very Short Echo Times", Schmalbrock et al., Radiology 1990, vol. 175, pp. 861–865.
"Three Dimension (Volume) Gradient-Echo Imaging of the Carotid Bifurcation: Preliminary Clinical Experience", Masaryk et al., Radiology 1989, vol. 171, pp. 801–806.
"Gadolinium-enhanced Magnitude Contrast MR Angiography of Popliteal and Tibial Arteries", Lossef et al., Radiology 1989, vol. 184, pp. 349–355.
"Intracranial Circulation: Preliminary Clinical Results with Three-Dimensional (Volume) MR Angiography", Masaryk et al., Radiology 1989, vol. 171, pp. 793–799.
"Contrast Enhancement in Abdominal CT: Bolus us. Infusion", Burgener, et al., AJR, vol. 137, pp. 351–358, 1981.
"Optimizing Blood Vessel Contrast in Fast Three-Dimensional MRI", Haacke, et al., SMRM Workshop on MR Imaging of Blood Flow, Mar. 13–14, 1989.
"Dynamic Gadolinium-Enhanced 3DFT Abdominal MR Arteriography", Prince et al.
"Abdominal Aorta and Renal Artery Stenosis: Evaluation with MR Angiography", Kim, et al., Radiology, vol. 174, pp. 727–731, Mar. 1990.
"Intracranial Vascular Lesions: Optimization and Clinical Evaluation of Thre-Dimensional Time-of-Flight MR Angiography", Marchal, et al., Radiology, vol. 175, pp. 443–448, May 1990.
"Normal Venous Anatomy of the Brain: Demonstration with Gadopentetate Dimeglumine in Enhanced 3-D MR Angiography", Chakeres, et al., AJR, vol. 156, pp. 161–172, Jan. 1991.

(List continued on next page.)

Primary Examiner—Lee S. Cohen
Assistant Examiner—Brian L. Casler
Attorney, Agent, or Firm—Neil A. Steinberg

[57] ABSTRACT

This invention is a method of imaging arteries distinctly from veins using nuclear magnetic resonance imaging in combination with intravenous administration of an magnetic resonance contrast agent. The contrast agent is intravenously injected in such a way that the arterial contrast concentration is substantially higher than the venous and background tissue concentration for a sufficiently long period of time to acquire the magnetic resonance image. The injection site of the contrast agent is chosen such that it is in a vein which is remote from the artery of interest. The magnetic resonance contrast agent may be intravenously infused at a variable infusion rate.

66 Claims, 6 Drawing Sheets

U.S. PATENT DOCUMENTS

| | | | |
|---|---|---|---|
| 4,915,111 | 4/1990 | Sano et al. | 128/653.3 |
| 5,010,191 | 4/1991 | Engelstad et al. | |
| 5,011,686 | 4/1991 | Pang. | |
| 5,034,694 | 7/1991 | Sattin et al. | |
| 5,055,288 | 10/1991 | Lewis et al. | |
| 5,078,986 | 1/1992 | Bosworth et al. | |
| 5,087,439 | 2/1992 | Quay | 424/9 |
| 5,141,740 | 8/1992 | Rajagopalan et al. | |
| 5,167,232 | 12/1992 | Parker et al. | |
| 5,190,744 | 3/1993 | Rocklage et al. | 128/653.3 X |
| 5,260,050 | 11/1993 | Ranney | 128/653.4 X |
| 5,305,751 | 4/1994 | Chopp et al. | 128/654 |
| 5,315,997 | 5/1994 | Widder et al. | 128/653.3 |

OTHER PUBLICATIONS

"Three-dimensional Time-of-Flight MR Angiography: Applications in the Abdomen and Thorax", Lewin, et al., *Radiology*, vol. 179, No. 1, pp. 261-264, Apr. 1991.

"Safety of Gadolinium-DPTA: Extended Clinical Experience", Niendorf, et al., *SMRM Workshop on Contrast Enhanced Magnetic Resonance*, May 23-25, 1991.

"Fast Time-of-Flight MR Angiography with Improved Background Suppression", Edelman, et al., *Radiology*, vol. 179, pp. 867-870, Jun. 1991.

"Normal Abdominal Enhancement Patterns with Dynamic Gadolinium-enhanced MR Imaging", Mirowitz, et al., *Radiology*, vol. 180, No. 3, pp. 637-640, Sep. 1991.

"Experience with High-Dose Gadolinium MR Imaging in the Evaluation of Brain Metastases", Yuh, et al., *AJNR*, vol. 13, pp. 335-345, Jan./Feb. 1992.

"Frequency Dependence of Tissue Relaxation Times", Bottomly.

"Assessment of Carotid Artery Stenosis by MR Angiography: Comparison with X-ray Angiography and ColorCoded Doppler Ultrasound", Anderson, et al., *AJNR* vol. 13, pp. 989-1003, May/Jun. 1992.

"Gadolinium-enhanced High-Resolution MR Angiography with Adaptive Vessel Tracking: Preliminary Result in the Intracranial Circulation", Lin, et al., *JMRI*, vol. 2, pp. 277-284, May/Jun. 1992.

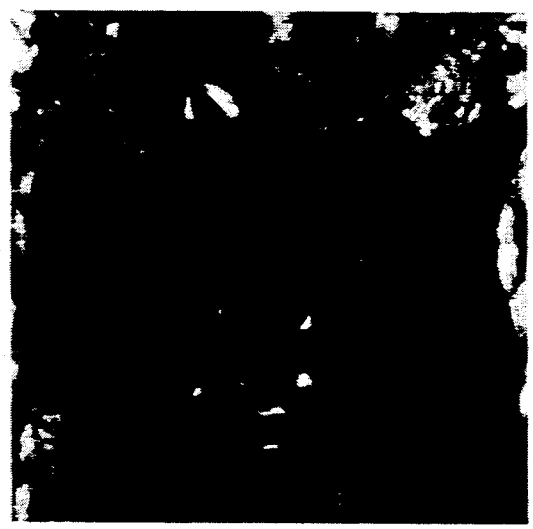
FIG. 6a — PRE GADO
FIG. 6b — DURING GADO INFUSION
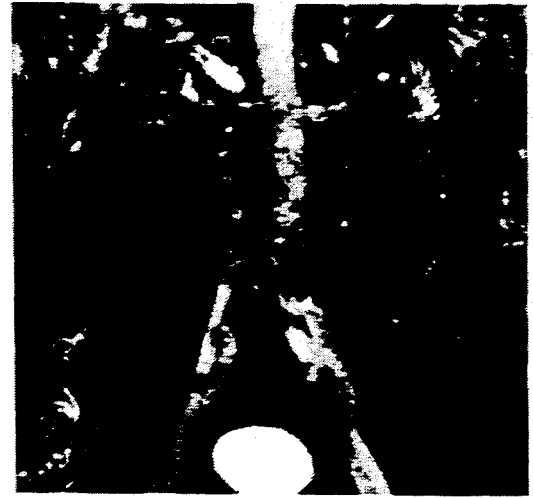
FIG. 6c — POST GADO

MAGNETIC RESONANCE ARTERIOGRAPHY WITH DYNAMIC INTRAVENOUS CONTRAST AGENTS

It is hereby noted that work associated with reducing this invention to practice was supported, in part, by the National Institutes of Health, under Grant No. HL 46384. The United States Government may retain certain rights in this invention.

BACKGROUND OF THE INVENTION

This invention relates to a method of magnetic resonance angiography to detect, diagnose, and treat arterial diseases and injuries. Arterial diseases and injuries are common and often have severe consequences including death. Imaging arteries serves to detect and characterize arterial disease before these consequences occur.

A conventional method of arterial imaging includes inserting a catheter into the artery of interest (the artery under study) and injecting radiographic contrast, for example, an iodinated contrast, while taking radiographs of the artery. Radiographs are commonly referred to as X-rays. In this technique, the contrast remains in the arteries for a few seconds during which the arteries appear distinct from both the veins and background tissue in the radiographs.

Although a catheter-based contrast arteriography technique generally provides high quality arterial images, there is a risk of arterial injury or damage by the catheter and its insertion. There may be thrombosis, dissection, embolization, perforation or other injury to the artery itself. Furthermore, such a technique may result in a stroke, loss of a limb, infarction or other injury to the tissue supplied by the artery. In addition, hemorrhage at the catheter insertion or perforation sites may require blood transfusions. Moreover, kidney failure and brain injury may result from the toxic effects of the X-ray contrast.

More recent techniques of arterial imaging are based upon detecting the motion of the blood within the arteries and/or veins. These techniques involve employing magnetic resonance imaging (MRI) to image moving blood distinct from stationary background tissues. (See, e.g., Potchen, et al., eds., "Magnetic Resonance Angiography/Concepts and Applications" Mosby, St Louis, 1993; the text of which is incorporated herein by reference). Such techniques do not necessitate catheter insertion into the artery. These techniques are commonly known as 2D time-of-flight, 3D time-of-flight, MOTSA, magnitude contrast, phase contrast, and spin echo black blood imaging.

With pre-saturation pulses it is possible to primarily image blood flowing in one direction. Since arteries and veins generally flow in opposite directions, these pre-saturation pulses allow preferential visualization of the arteries or the veins. Because these techniques depend upon blood motion, the images are degraded in patients who have arterial diseases which decrease or disturb normal blood flow. Such types of arterial diseases that decrease or disturb normal blood flow include aneurysms, arterial stenoses, arterial occlusions, low cardiac output and others. The resulting lack of normal blood flow is particularly problematic because it is those patients with disturbed blood flow in whom it is most important to acquire good quality arterial images.

A related magnetic resonance imaging technique relies upon differences in the proton relaxation properties between blood and background tissues. (See, e.g., Marchal, et al., in Potchen, et al., eds., supra, pp. 305–322). This technique does not depend upon steady blood in-flow. Instead, this magnetic resonance imaging technique involves directly imaging the arteries after administering a paramagnetic contrast agent. Here, after administering the contrast agent, it is possible to image arteries directly based upon the blood relaxation properties. This technique overcomes many of the flow related problems associated with magnetic resonance imaging techniques which depend upon blood motion.

Several experts have performed magnetic resonance arterial imaging using intravenous injection of gadolinium chelates (paramagnetic contrast agents). These experts have reported their results and conclusions. In short, these results have been disappointing and, as a result, the use of gadolinium for imaging arteries has not been adopted or embraced as a viable arterial imaging technique. The images using this technique are difficult to interpret because the gadolinium tends to enhance both the arteries and the veins. Since the arteries and veins are closely intertwined, it is extremely difficult to adequately evaluate the arteries when the veins are visible. Further, the difficulty in interpretation is exacerbated as a result of contrast leakage into the background tissues.

As a result, there exists a need for an improved method of magnetic resonance angiography which provides an image of the arteries distinct from the veins and which overcomes the limitations of other techniques.

SUMMARY OF THE INVENTION

In a first principal aspect, the present invention is a method of imaging an artery in a patient, for example, a human or other animal, using magnetic resonance imaging, including, administering a magnetic resonance contrast agent to said patient, by intravenous infusion in a vein remote from the artery, substantially throughout acquisition of magnetic resonance image data and at an infusion rate sufficient to provide contrast enhancement of said artery relative to veins and background tissue in the field of view of the magnetic resonance image. In a preferred embodiment, the magnetic resonance contrast agent is intravenously injected at a variable infusion rate during the period of acquisition of image data.

In another preferred embodiment, the magnetic resonance contrast agent is paramagnetic. In this embodiment, the paramagnetic contrast agent may be intravenously infused at a rate of greater than 0.0015 liters/kilogram-second$^2$ divided by the relaxivity of the paramagnetic contrast agent. Further, the paramagnetic contrast agent may be intravenously infused at a rate greater than 0.0025 liters/kilogram-second$^2$ divided by the relaxivity of the paramagnetic contrast agent.

In a preferred embodiment, the paramagnetic contrast agent is a gadolinium chelate. Under this circumstance, the dose of the gadolinium chelate may be within the range of 0.05 millimoles/kilogram body weight to 0.7 millimoles/kilogram body weight. Further, the dose of the gadolinium chelate may be within the range of 0.15 millimoles/kilogram body weight to 0.35 millimoles/kilogram body weight.

In another preferred embodiment, the magnetic resonance contrast agent is administered manually through a fluid flow restrictor. In this embodiment, the fluid flow restrictor is coupled to a vessel containing the magnetic resonance contrast agent wherein the amount of magnetic resonance contrast agent in said vessel is substantially equal to the amount dispensed during the period of acquisition of image data.

In another preferred embodiment, the magnetic resonance contrast agent is administered by a mechanical injector. In this embodiment, the mechanical injector is adapted to receive a vessel containing said magnetic resonance contrast agent. In an alternative embodiment, the mechanical injector is coupled to a vessel containing said magnetic resonance contrast agent.

In a preferred embodiment, the magnetic resonance contrast agent is a paramagnetic contrast agent and the magnetic resonance image data acquisition uses a 3D Fourier transform gradient echo pulse sequence with $TR \leq 30$ milliseconds, the flip angle is between 20° and 9°, and the field of view is between 5 and 40 centimeters, with between 20 and 90 partitions of partition thickness of between 0.5 and 3 millimeters.

In another embodiment, before administration of said magnetic resonance contrast agent, a first image is acquired and, during administration of said magnetic resonance contrast agent, a second image is acquired and wherein a final image is enhanced by subtracting the first image from the second image.

EKG gating may be applied during acquisition of image data to reduce cardiac motion artifacts. Further, respiratory compensation may be applied during acquisition of image data to reduce respiratory motion artifacts. In addition, the patient may be premedicated before acquisition of image data to reduce the heart rate, the respiratory rate, or the cardiac output.

In another principal aspect, the present invention is an infusion apparatus for infusing a magnetic resonance contrast agent into a vein of a patient to enhance a magnetic resonance image of an artery of said patient wherein said artery is remote from said vein. The infusion apparatus includes a vessel containing magnetic resonance contrast agent and infusion means, coupled to said vessel, for infusing said magnetic resonance contrast agent into said vein of said patient substantially throughout the period of acquisition of image data and at an infusion rate sufficient to provide contrast enhancement of an image of an artery relative to veins in the field of view of the magnetic resonance image.

In a preferred embodiment, the infusion means is a mechanical injector which is adapted to receive said vessel containing said magnetic resonance contrast agent. In another preferred embodiment, the magnetic resonance contrast agent is administered at a variable rate during the period of acquisition of image data.

In yet another principal aspect, the present invention is a method of imaging an artery in a patient using magnetic resonance imaging, including, administering a gadolinium chelate to the patient by substantially continuous intravenous infusion, in a vein remote from the artery, throughout the period of acquisition of image data and at an infusion rate greater than 0.0015 liters/-kilogram-second$^2$ divided by the relaxivity of the gadolinium chelate.

In a preferred embodiment, the gadolinium chelate is administered manually through a fluid flow restrictor. The fluid flow restrictor may be coupled to a vessel containing an amount of the gadolinium chelate substantially equal to the amount dispensed during the period of acquisition of image data.

In another preferred embodiment, the gadolinium chelate is administered by a mechanical injector. The mechanical injector may be adapted to receive a vessel containing said gadolinium chelate. Alternatively, the mechanical injector may be coupled to a vessel containing said gadolinium chelate.

The present invention overcomes the limitations of other techniques by injecting magnetic resonance contrast agents at a sufficient rate for an appropriate duration in such a way that the contrast level in the arteries is higher than the venous level in veins of the region being visualized for the period of magnetic resonance imaging. The injection is performed intravenously in a vein which is remote from the artery of interest. Intravenous injection eliminates the risks associated with arterial catheterization. In the present invention, the high level of arterial contrast permits directly imaging the arterial lumen, analogous to conventional arteriography. By using a magnetic resonance pulse sequence that is not as sensitive to motion, it reduces the flow artifacts associated with phase contrast or magnitude contrast (time-of-flight) magnetic resonance angiography.

The present invention is a method of magnetic resonance angiography which combines several of the advantages of catheter-based contrast arteriography with the advantages of magnetic resonance imaging while substantially eliminating the disadvantages of each.

BRIEF DESCRIPTION OF THE DRAWINGS

In the course of the detailed description of preferred embodiments to follow, reference will be made to the attached drawings, in which:

FIG. 6 illustrates typical coronal maximum intensity projection (MIP) collapse images obtained (a) prior to injection of gadopentetate dimeglumine, (b) dynamically during intravenous injection of gadopentetate dimeglumine, 0.2 millimoles/kilogram over 5 minutes and (c) immediately following injection of gadopentetate dimeglumine;

DESCRIPTION OF A PREFERRED EMBODIMENTS

Figure 1:
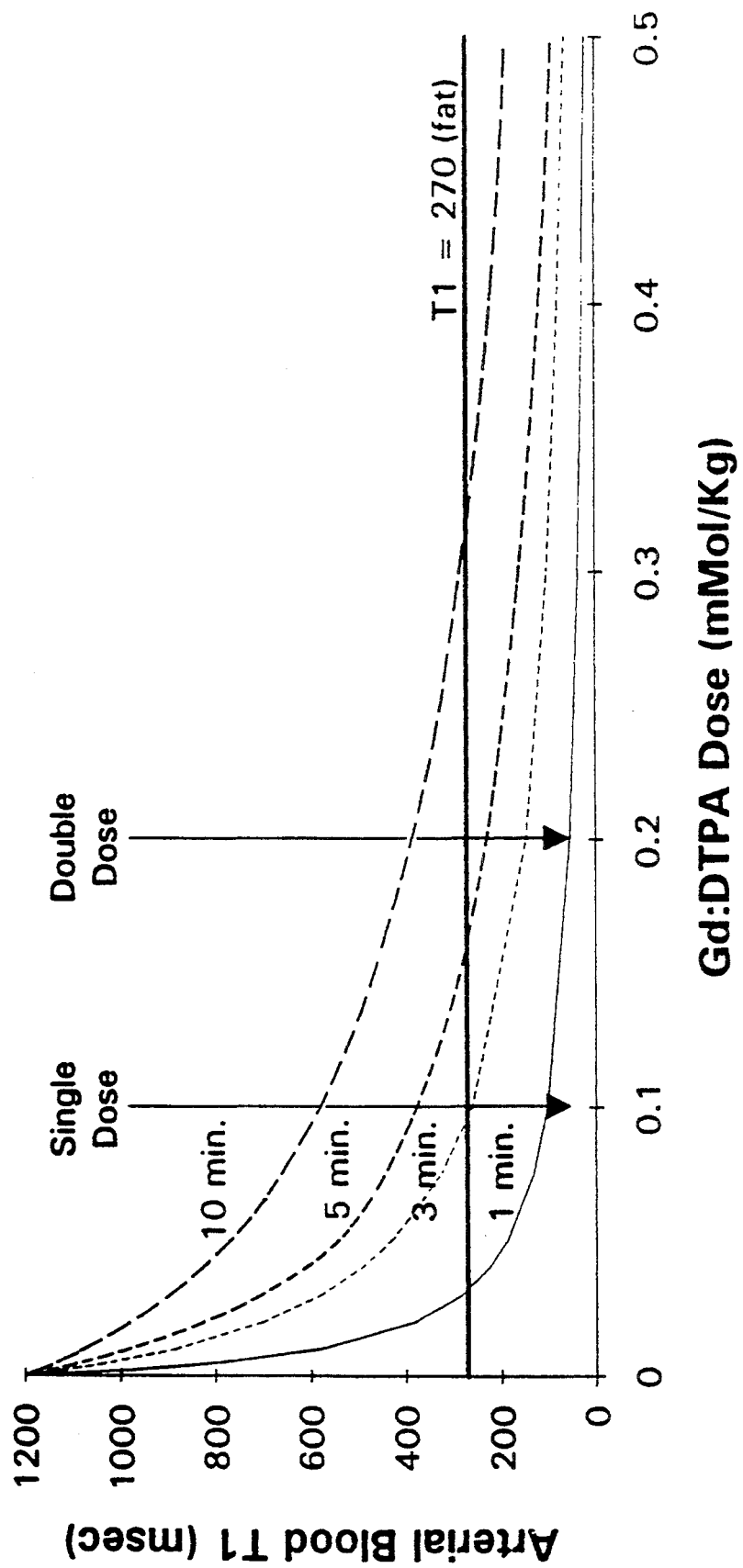
FIG. 1 illustrates longitudinal relaxation time (T1) of blood as a function of injection imaging time and total paramagnetic contrast dose for a compound with a relaxivity of 4.5/millimolar-second.

The present invention is a method of magnetic resonance angiography wherein the magnetic resonance imaging data is collected over a period with simultaneous controlled intravenous injection of a magnetic resonance contrast agent. The magnetic resonance contrast agent is preferably injected into a patient, for example, a human or other animal, substantially throughout the period of imaging in a controlled manner, i.e., injected at a controlled rate over the period of imaging. In a preferred embodiment, the magnetic resonance contrast agent is administered as a steady and continuous infusion in a vein which is remote from the artery of interest, i.e., artery under study.

The method of this invention is especially useful in imaging peripheral arteries. A peripheral artery is an artery that is outside the brain. Since the blood-brain barrier prevents redistribution of the contrast agent from the capillary bed in the brain, this invention is more effective in imaging arteries found in a patient's body which are below the neck.

Magnetic resonance contrast agents employed when implementing the present invention are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds. Gadopentetate dimeglumine and gadoteridol are two paramagnetic gadolinium chelates that are readily available, and which rapidly redistribute into the extracellular fluid compartment. Other gadolinium compounds are acceptable, and may have a higher relaxivity, more rapid redistribution into the extracellular fluid compartment, and greater and faster extraction in the capillary bed. It should be noted that, contrast agents that are extracted or degrade in or near the capillary bed are preferred for the present invention.

In a preferred embodiment, the injected magnetic resonance contrast agent should be sufficiently small to rapidly redistribute into the extracellular fluid compartment in the systemic capillary bed, or the contrast agent should be actively extracted from the circulation in the capillary bed distal to the artery of interest, or both. Under these circumstances, the artery (or arteries) of interest contain a high concentration of contrast and the vein (or veins) adjacent to the artery (or arteries) of interest possess a low contrast concentration. Further, under these circumstances, the relationship of artery-to-venous contrast concentration is substantially maintained over the period of contrast injection.

By matching the duration of the injection with the time required for a longitudinal relaxation time (T1) weighted magnetic resonance image data set, it is possible to view the arteries distinct from the veins. Further, by injecting the contrast at a sufficient rate, the longitudinal relaxation time of the arterial blood may be made sufficiently short when compared to that of the background tissues. As a result, the image of the arteries is distinct from background tissue as well.

As mentioned above, the magnetic contrast agent is administered to the patient, for example, a human or other animal, via intravenous infusion, i.e., injection into a patient at a controlled rate over a period of time. Preferably the period of infusion for magnetic resonance contrast agent according to this invention will be all or a substantial portion of the time during which image data is being collected for a magnetic resonance image. A substantial portion of the data collection time is at least a majority of the time, usually at least 75% of the collection period, and preferably greater than 85% of the collection period.

The rate of infusion of the magnetic resonance contrast agent is controlled so that the amount of contrast agent infused will result in a concentration difference over a substantial portion of the duration of image data collection between the arteries and any background tissue in the field of view, including veins, which will cause enhancement of the arteries in the final image relative to background, and especially relative to the veins which appear in the field of view.

In those instances where the invention is implemented using paramagnetic contrast agents, infusion is at a rate that will provide a concentration of the agent in the arteries, such that the arteries will appear at least 50% brighter than any background structure, including veins, in the final image. In a preferred embodiment, the concentration of contrast agent will cause the longitudinal relaxation time (T1) of the water protons in the arteries to be shorter than protons in any of the background material. Where the contrast agent causes the arteries to appear black in the final image (e.g., where the contrast agent shortens T2*, for example, Fe powder), the contrast agent should be infused at a rate and amount to insure that the effective transverse relaxation time (T2*) in the arteries is shorter than in any of the background material.

Any apparatus suitable for magnetic resonance imaging (MRI) of a portion of an animal body, for example, a human, may be used for acquisition of image data in the method of this invention. In particular, apparatus and imaging methods for magnetic resonance angiography (MRA) are known in the art (see, e.g., U.S. Pat. Nos. 4,718,424; 5,034,694; and 5,167,232, incorporated herein by reference), and these may be used with the method of MRA with dynamic intravenous injection of magnetic resonance contrast agents taught herein, subject only to the constraints taught below.

The parameters of the imaging method of the present invention are discussed immediately below with respect to gadolinium chelates. It should be noted that other magnetic resonance contrast agents may be employed in practicing the present invention including paramagnetic contrast agents, such as those described by Marchal, et al., in Potchen, et al., eds., supra, pp. 305–322, the text of which is incorporated herein by reference.

Injection Parameters

Gadolinium chelates are paramagnetic agents which shorten the longitudinal relaxation time, T1, of blood according to EQUATION 1:

$$\frac{1}{T1} = \frac{1}{1200} + \text{Relaxivity} \times [Gd] \qquad (1)$$

where:
(1) the longitudinal relaxation time (T1) of blood without gadolinium is 1200 ms; and
(2) [Gd] is the blood concentration of a gadolinium chelate.

As reflected in EQUATION 2, the arterial blood [Gd] may be expressed in terms of the intravenous injection rate and the cardiac output during dynamic imaging at times short as compared to the recirculation time.

$$[Gd]_{arterial} = \frac{\text{Injection Rate}}{\text{Cardiac Output}} + [Gd]_{venous} \quad (2)$$

As long as the gadolinium chelate is sufficiently small, the gadolinium chelate will rapidly redistribute into the extracellular compartment as it passes through the capillary bed and the venous concentration will be low or negligible compared to the arterial concentration. The relationship between the longitudinal relaxation time of arterial blood and the injection rate may then be determined by combining EQUATION 1 and EQUATION 2, as stated below in EQUATION 3:

$$\text{Injection Rate} = \frac{\left[\frac{1}{T1} - \frac{1}{1200}\right]}{\text{Relaxivity}} \times \text{cardiac output} \quad (3)$$

To achieve contrast between arterial blood and background tissue, the longitudinal relaxation time of the arterial blood should be reduced to less than that of the background tissues. Of all types of background tissues, fat (T1=270 msec) typically has the shortest longitudinal relaxation time. Assuming a typical minimum resting cardiac output of 0.0005 Liters/Kg-sec and requiring the longitudinal relaxation time to be less than 270 milliseconds simplifies EQUATION 3 to:

$$\text{Injection Rate} > \frac{0.0015 \, L/Kg - \sec^2}{\text{Relaxivity}} \quad (4)$$

By way of example, gadopentetate dimeglumine and gadoteridol are two paramagnetic gadolinium chelates that are readily available and rapidly redistribute into the extracellular fluid compartment. The relaxivities of gadopentetate dimeglumine and gadoteridol are 0.0045/molar-second. Based upon the aforementioned, using EQUATION 4, the minimum injection rate is greater than 0.033 millimoles/kilogram-minute.

The total dose of gadolinium chelate required may be determined by multiplying the injection rate by the imaging time. For a relaxivity of 4.5/millimolar-second, and an imaging time of 5 minutes (300 seconds), the dose should substantially exceed 0.1 millimoles/kilogram.

The dose of the gadolinium chelate may be within the range of 0.05 millimoles/kilogram body weight to 0.7 millimoles/kilogram body weight depending upon the time required to obtain the image. It should be noted that the dose of the contrast should not be too high such that there may be undesirable toxicity or T2 effects. In a preferred embodiment, the dose of the gadolinium chelate is within the range of 0.15 millimoles/kilogram body weight to 0.35 millimoles/kilogram body weight. In a more preferred embodiment, the dose of the gadolinium chelate is about 0.25 millimoles/kilogram body weight.

In those instances where the contrast injection times are longer than the recirculation time, the longitudinal relaxation time of arterial blood tends to be even shorter since a fraction of the gadolinium chelate will recirculate. It should be noted that a T1 of 270 ms (corresponding to the brightest background tissue fat) is equivalent to a gadopentetate dimeglumine concentration of 0.6 millimoles/liter.

FIG. 1 illustrates the longitudinal relaxation time (T1) of blood as a function of infusion time and the total paramagnetic contrast dose for a paramagnetic contrast compound having a relaxivity of 4.5/millimolar-second. An examination of FIG. 1 reveals that the shortest T1 occurs with the shortest infusion time and the largest gadolinium dose. For typical imaging times of 3 to 5 minutes, FIG. 1 further reveals that the dose should be of the order of 0.2 millimoles/kilogram or larger in order to achieve a longitudinal relaxation time of blood significantly shorter than that of the brightest background tissue fat (T1=270) for the entire duration of imaging.

Imaging Parameters

Any suitable T1 weighted magnetic resonance imaging sequence may be used during injection of the paramagnetic contrast. Suitable imaging sequences will be readily apparent to the skilled practitioner and are described in Potchen, et al., eds., supra. The following criteria for selection of preferred imaging parameters are based on experience in over 100 patients on a 1.5 Tesla General Electric signa magnet with version 4.7 software. A three-dimensional Fourier Transform (volume) acquisition (3D FT) is preferred in the abdomen because of its intrinsically high spatial resolution and high signal-to-noise ratio, even with a large, body coil. The gradient echo (gradient recalled) pulse sequences are preferred since they allow a short TR (repetition time) which allows a shorter imaging acquisition time. Short imaging times have the advantage of allowing the same total gadolinium dose to be injected at a faster rate.

Spoiled Versus Non-spoiled Gradient Echo Imaging

It should be noted that one might expect steady gradient echo imaging (GRASS) to be preferable to the spoiled gradient echo imaging because the long T2 (transverse relaxation time) of blood increases the steady state blood signal. However, this effect enhances veins more than arteries, because the fast pulsatile flow of arterial blood spoils its steady state component. In theory, this may have the paradoxical effect of reduced arterial contrast. In practice, there may only be a small difference between the spoiled and unspoiled techniques. A spoiled gradient echo pulse sequence (SPGR) was chosen for most of the studies described herein to simplify the theory and analysis to reduce the potential for differential steady state magnetization between arterial blood, slower venous blood and background tissue.

Echo Time

Because the brightest background tissue is fat, it is preferable to use a TE (echo time) where fat and water are out of phase, thereby achieving an incremental improvement in vessel-to-background contrast. At 1.5 Tesla, this occurs every 4.6 msec beginning at 2.3 msec which corresponds to a TE of 2.3, 6.9, 11.5, . . . milliseconds. The shortest of these possible TE values (6.9 msec. in the studies described herein) is preferred. Shorter TE's tend to minimize the effects of motion related phase dispersion.

Repetition Time

In a preferred embodiment, TR should be as short as is possible. A TR of 24–25 msec was the shortest possible on the equipment used for the studies described herein. As the TR is shortened, the flip angle must be adjusted to maintain the optimal T1 weighing.

Flip Angle

With a gadolinium chelate dose of 0.2 millimoles/-kilogram and a 3–5 minute injection imaging time, the longitudinal relaxation time of the arterial blood is predicted to be in the order of 150 to 200 milliseconds. It will, however, be shorter as a result of the recirculation time being less than 3–5 minutes. The relative signal intensity, SI, in a 3D FT spoiled gradient echo acquisition as a function of blood T1, TR, T2, T2*, flip angle e, and proton density N(H) may be expressed as stated in EQUATION 5, and calculated accordingly.

$$SI = N(H) = \frac{1 - \exp\left(-\frac{TR}{T1}\right)}{1 - \cos(\alpha)\exp\left(-\frac{TR}{T1}\right)} \sin(\alpha) \exp\left(-\frac{TE}{T2^*}\right) \quad (5)$$

Figure 2:
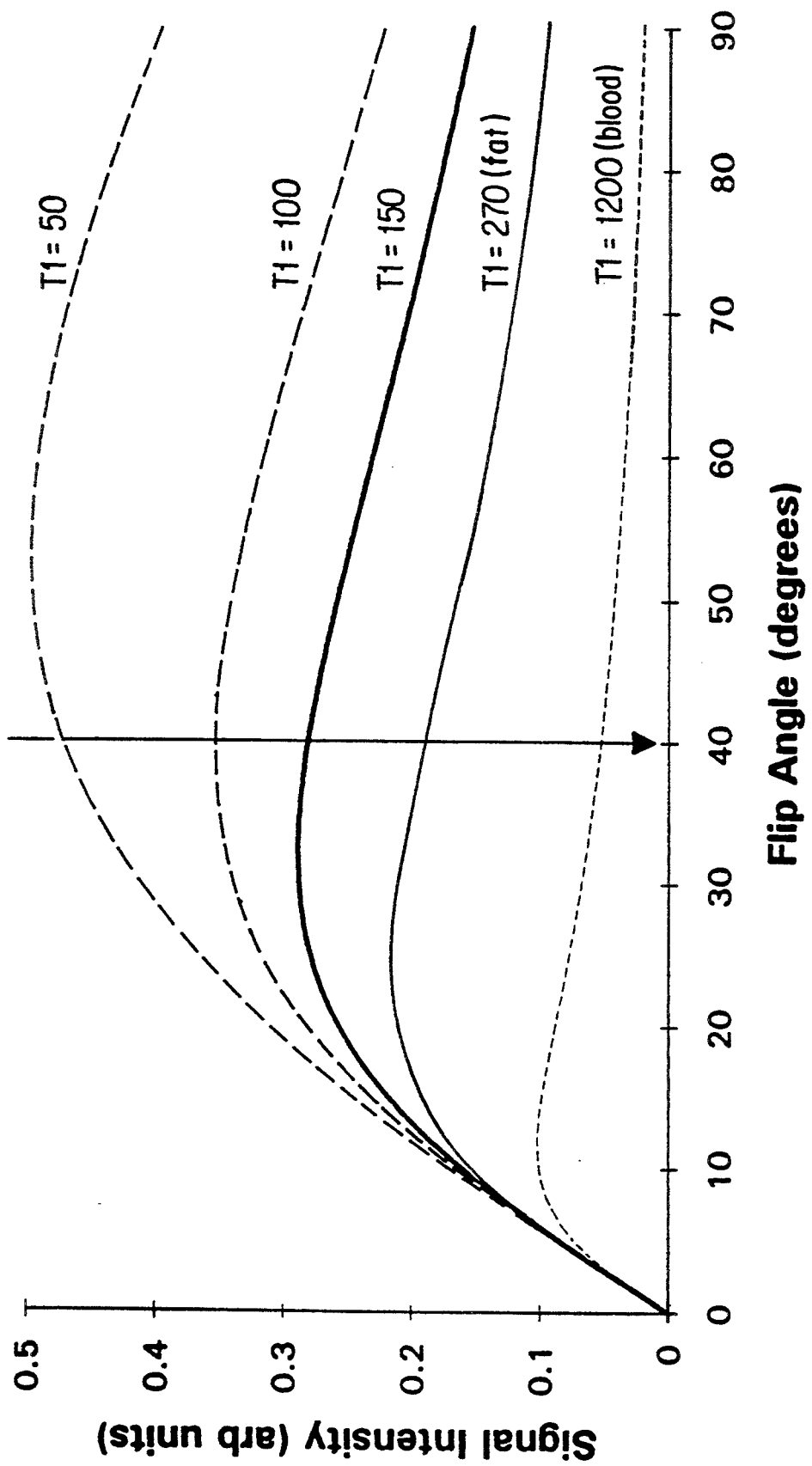
FIG. 2 illustrates calculated magnetic resonance signal intensity as a function of flip angle for 5 different longitudinal relaxation times (T1) assuming a spoiled, 3D volume acquisition with TR equal to 25 msec and $TE<<T2^*$.

FIG. 2 graphically illustrates relative signal intensity for T1 equal to f50, 100, 150, 270 (fat), and 1200 (blood) under the following conditions: (1) TR=25 milliseconds, and assuming TE is small compared to T2* (the observed transverse relaxation time). FIG. 2 reveals that a flip angle of about 40 degrees is optimal for maximizing blood-to-background tissue (fat) contrast when the longitudinal relaxation time (T1) of blood is of the order of 200 milliseconds. For larger gadolinium doses with faster injection rates, a larger flip angle may be more appropriate.

Volume Orientation

In order to minimize the image acquisition time, the imaging volume should be made as thin as possible while containing the arteries of interest. In this regard, it may be useful to orient the image volume for maximum in-plane coverage of the vessels of interest as opposed to the perpendicular orientation required for optimal time-of-flight magnetic resonance angiography (MRA). Optimizing the orientation and minimizing the thickness of the imaging volume is facilitated by first acquiring a conventional black-blood or time-of-flight MRI to use as a guide for precise localization. Phase and frequency encoding axes should be oriented such that cardiac and respiratory motion artifacts do not superimpose on the vessels of interest. Generally, for imaging the aorta-iliac system, the imaging volume should be oriented coronally, and the phase encoding axis should be set right-to-left.

Partitions

The number of partitions is determined by the thickness of the image volume divided by the partition thickness. The partition thickness is the image resolution along the axis perpendicular to the plane of the partitions. It may be useful to employ thin partitions in order to have high image resolution. The image acquisition time, however, linearly increases with the number of partitions. As a result, keeping the image acquisition time short requires minimizing the number of partitions.

It should be noted that there may be a loss of signal-to-noise as the voxel size is decreased by using higher resolution pixels. Generally, 0.5 to 2 millimeter resolution with 28 to 60 partitions is adequate for the aorta and major branch vessels. The skilled practitioner will balance the need to increase resolution by decreasing voxel size with the need to avoid excessive periods of time to acquire image data.

Field-of-View

The field-of-view must be made large enough to avoid excessive wrap-around artifact. Wrap around artifacts occur when there are structures outside the field of view along the phase encoding axis. These structures are mapped by the phase encoding process to superimpose on structures within the field of view.

In addition, because of the limited number of pixels along the frequency encoding axis and time penalty for each additional pixel along the phase encoding axis, it is also desirable to make the field-of-view as small as possible in order to maximize image resolution with the minimum image acquisition time. Generally, for imaging the abdominal or thoracic aorta, a field-of-view of about 36 centimeters is appropriate for most patients. It may be increased for larger patients and reduced for smaller patients. Smaller field-of-views may be used for other parts of the body.

Use of a no-phase wrap algorithm is a less preferred embodiment. Under the circumstance of this invention, this has a disadvantage of generally requiring more imaging time and, as a result, a larger gadolinium dose.

Coils

It is preferable to use the smallest possible coil in order to minimize noise. There is also an advantage to coils that encircle the body part of interest so that the signal will be homogeneous throughout the entire field-of-view.

Patient Positioning

The patient should be positioned such that the body part being imaged will remain stationary, i.e. hold still, over the duration of the image acquisition.

Cardiac Gating and Respiratory Compensation

The phase artifact related to respiratory and cardiac motion may be minimized by combining the T1 weighted imaging sequence with respiratory compensation and/or electrocardiographic gating. Gating has the disadvantage of increasing the scan time—particularly in patients with irregular rhythms. Compensation techniques in which the acquisition of the image data in k-space is matched to the respiratory and or cardiac cycle may eliminate some phase artifact without significantly increasing the scan time.

Pre-scanning

The pre-scanning process is used to tune to the optimum frequency and to optimize the receiver gain. In the pre-scanning process, it is necessary to compensate for the changes in the patient's magnetic resonance signal that will occur during the contrast injection. In those instances when the paramagnetic contrast agent is a gadoliniumchelate, it is preferable to tune to the water peak. About a 20% to 50% margin should be incorporated into the receiver gain setting to allow for increased signal during contrast administration.

Premedication

Premedicating patients with an analgesic or sedative such as diazepam may be useful for at least two reasons. Firstly, it may help the patient to tolerate the claustrophobic sensation of being within the magnet thereby reducing voluntary motion artifacts. Secondly, and more importantly, its relaxation and cardiac depressant effects tend to reduce the cardiac output. A lower cardiac output results in a higher arterial contrast concentration which thereby improves the image quality. This result is opposite from conventional magnetic resonance angiography which is degraded when the cardiac output decreases. By reducing the cardiac and respiratory rates, analgesics and sedatives may minimize the fraction of the image acquisition that is adversely affected by cardiac and respiratory motion artifacts.

Magnetic Resonance Contrast Agents

As mentioned above, many different magnetic resonance contrast agents may be employed when implementing the present invention; for example, numerous paramagnetic contrast agents are suitable. As mentioned above, gadolinium compounds, for example, paramagnetic gadolinium chelates, such as gadopentetate dimeglumine and gadoteridol, are readily available and rapidly redistribute into the extracellular fluid compartment. Other gadolinium compounds are acceptable. In general, preferred contrast agents have a high relaxivity, rapid redistribution into the extracellular fluid compartment, and are readily extracted from the capillary bed. It should be noted that, contrast agents that are extracted or degrade in the capillary bed are preferred in the present invention.

Injection

In a preferred embodiment, the type or form of injection of the paramagnetic contrast is intravenous. The injection of the paramagnetic contrast is performed intravenously in order to eliminate or reduce the complications associated with the catheterization required for arterial injections.

The specific site of injection is important for several reasons. The site of injection should be remote from the "region of interest"; that is, the region that is to be scanned. For example, when imaging the abdominal aorta, intravenous injection of the paramagnetic contrast into an arm vein is preferred. Use of a leg vein should be avoided. Further, there may be some benefit in avoiding the antecubital fossa because the patient may bend the elbow during a long (3–5 minute) period of injection which may result in extravasation of the contrast into the subcutaneous tissues. As a result, under this condition, a forearm vein may be preferable.

In those instances where an artery in the arm is to be imaged, the site of the injection may be a leg vein or a vein the opposite arm. Here, the site of injection is remote from the "region of interest" i.e., the artery in the arm.

Figure 3:
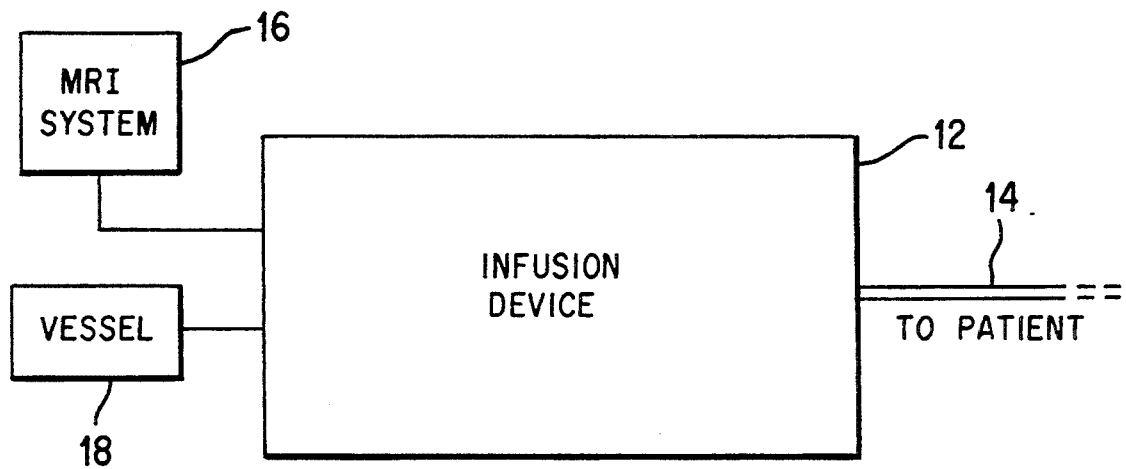
FIGS. 3 and 4 are block diagram representations of mechanical infusion devices and configurations, according to the present invention.
Figure 4:
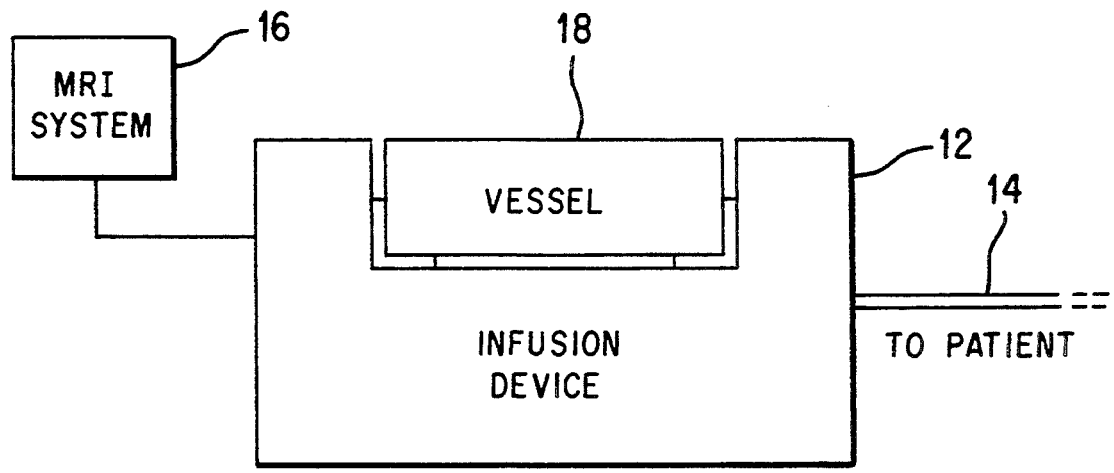

In a preferred embodiment, as illustrated in FIGS. 3 and 4, a mechanical infusion or injection device 12 is an automated type of injector having reliable and consistent operating conditions. The infusion device 12 is employed to inject the magnetic resonance contrast agent into the vein of the patient at an infusion rate sufficient to provide contrast enhancement of an image of an artery relative to veins in the field of view of the magnetic resonance image and substantially throughout the period of acquisition of image data. The infusion device 12 couples to the patient using convention techniques, for example, appropriately selected tubing 14 which permits fluid flow between the mechanical infusion device 12 and the patient. Such tubing may be, for example, an angiocatheter.

A mechanical injector is preferred because of the greater reliability and consistency when compared to injecting by hand. Since the magnetic field interferes with normal functioning of electronic devices, a pneumatic powered, spring loaded or other non-electric pump may be suitable. It should be noted, however, that an electrical pump may be used if its operation is unaffected by the operation of the magnetic resonance imaging system, e.g., if the pump is adequately shielded or if it is located sufficiently far from the magnet.

In one preferred embodiment, the mechanical infusion device 12 is coupled to the magnetic resonance imaging system 16 to facilitate proper or desired timing between the injection of the magnetic resonance contrast agent and the acquisition of the image data, in addition to providing proper or desired rates of infusion of the contrast agent.

In another preferred embodiment, proper or desired timing and rates of infusion of the contrast agent are controlled through a control mechanism at the mechanical infusion device 12. That is, the mechanism that controls the infusion timing and rates of infusion is implemented within the mechanical infusion device 12. In this circumstance, the mechanical infusion device 12 is a "self-contained" unit.

As mentioned above, the infusion device 12 injects the magnetic resonance contrast in a strictly controlled manner. The contrast may be contained in a vessel. As illustrated in FIG. 3 and 4, the mechanical infusion device 12 is coupled to a vessel 18 which contains the magnetic resonance contrast agent. In one embodiment, the vessel 18 may contain a sufficient quantity of contrast agent for one application of the invention, e.g., a single use vessel. In an alternative embodiment, the vessel 18 may contain a quantity which allows several applications of the invention, e.g., a reservoir type of vessel. As is illustrated in FIG. 3, the mechanical infusion device 12 may be adapted to receive the vessel 18 somewhat like a fountain pen receiving an ink cartridge. In an alternative embodiment, as illustrated in FIG. 4, the infusion device 12 may be coupled to the vessel 18 using conventional methods.

The precise timing of the injection of the paramagnetic contrast is important. The injection of the paramagnetic contrast agent should be confined to a period during which imaging data is being collected; that is to say, concurrent with the acquisition of image data. It is important that no contrast be administered prior to magnetic resonance scan since the contrast may leak into the background tissues and cause a degradation of the image. If some paramagnetic contrast or other magnetic resonance contrast has been administered prior to imaging, it is preferred to delay the arterial scan until this contrast has been excreted by the patient, in order to increase the probability of obtaining the optimal images.

The constant infusion should begin within a few seconds of initiation of the scan process. The contrast infusion should end about 20 seconds before the completion of the scan; this allows the intravenously injected contrast to circulate through the heart and into the arteries. A chaser of normal saline or other fluid may be used to insure injection of the entire dose of the paramagnetic contrast (e.g., gadolinium) and, in addition, to insure that there is sufficient venous return to propel the injected contrast to the heart. In a preferred embodiment, the injection rate for contrast is matched with the mapping of k-space so that the maximum injection rate occurs during acquisition of the center of k-space. This may permit injecting over a shorter period of time to achieve either a higher injection rate or a lower contrast dose.

Figure 5:
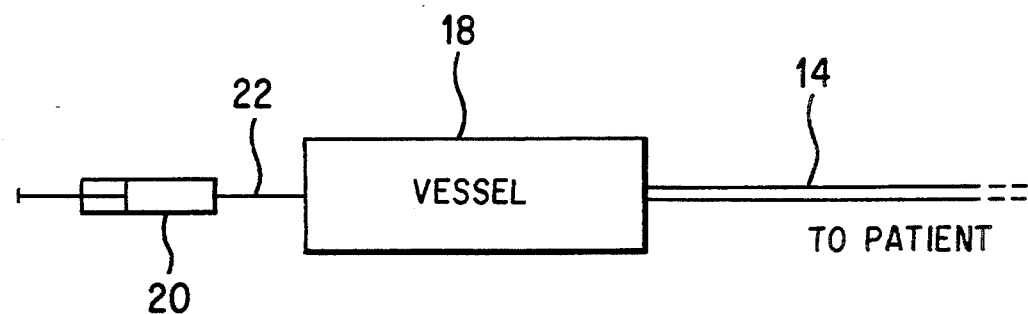
FIG. 5 is a block diagram representation of a manual injection configuration, according to the present invention.

With reference to FIG. 5, the infusion of the magnetic resonance contrast agent may be by way of manual means. In this embodiment, a syringe 20, having needle 22, is coupled to a vessel 14 containing the magnetic resonance contrast agent. The vessel 14 is coupled to the patient using conventional techniques, for example, appropriately selected tubing 14 which permits fluid flow between the vessel 18 and the patient, for example, an angiocatheter.

When implementing the present invention via manual injection, i.e., injecting the magnetic resonance contrast agent by hand, in a preferred embodiment, the infusion "path" includes a fluid flow restrictor which adds resistance to the flow of gadolinium during administration into the body. It should be noted that a fluid flow restrictor may be, for example, a standard injection needle or small calibre angiocatheter. In FIG. 5, the fluid flow restrictor may be the needle 22 of syringe 20 and/or the angiocatheter 14. Use of small needles or small calibre angiocatheters may alleviate errors of injecting the contrast too rapidly and, as a result, depleting or running-out of contrast before completion of the scan. In a preferred embodiment, the needle size may be 22 gauge or smaller diameter (greater than or equal to 22 gauge) depending upon the viscosity of the contrast agent.

It may be convenient to preload the contrast into a vessel or length of tubing with luer lock or other appropriate connectors at each end of the tubing. It is then possible to use a single saline filled syringe to inject the contrast followed by a saline chaser without having to switch syringes or pumps. Saline is a preferred fluid to use as a chaser since it can be made isotonic with blood and is compatible with most intravenous fluids and pharmaceuticals that may already be flowing through a patient's IV line.

In a preferred embodiment, the contrast is infused slowly at the beginning and fastest in the middle of the acquisition. This type of injection pattern, based upon the fact that the contrast does somewhat contribute to venous and background tissue enhancement, avoids excessive contrast early in the acquisition.

Post-Processing

Post-processing of the scan data may be used. Maximum intensity projection (MIP) collapse images are useful for rapidly examining the entire arterial circulation within the region of interest. It may be useful to reformat and selectively collapse the data through the specific arteries of interest. Additional contrast may be obtained by digitally subtracting a pre-gadolinium acquisition from the dynamic gadolinium acquisition. Volume rendering may also be useful and is possible with high contrast volume data sets.

Immediately below are examples of results obtained from use of preferred embodiments of the present invention. The parameters of the examples are detailed therein.

EXAMPLE 1

Contrast between peripheral arteries and veins in images obtained by imaging dynamically during the administration of gadopentetate dimeglumine was investigated in sixteen patients referred for aorta-iliac magnetic resonance arteriography. These included 9 males and 7 females with a mean age of 72 ranging from 67 to 83. The indications for the study included hypertension (6), abdominal aortic aneurysm (AAA, 6) claudication (4) and renal failure (9). Some patients had more than one indication.

Parameters

All imaging was performed on a 1.5 Tesla superconducting magnet (General Electric Medical Systems, Milwaukee, Wis.) using the body coil and version 4.7 software. A 3D FT, coronal, spoiled, gradient echo volume was acquired centered on the mid-abdomen. The imaging parameters included: 12 centimeters volume with 60 partitions, 2 millimeters partition thickness, TR of 25 milliseconds a TE of 6.9 milliseconds, a flip angle of 40°, first order flow compensation, 36 centimeters field of view, 256 by 192 matrix. The imaging time was 5 minutes and 10 seconds. Frequency was set superior to inferior so that phase artifact from diaphragmatic and cardiac motion would not superimpose on the abdominal aorta and IVC. When possible, phase artifact noise was minimized by excluding the heart and lungs entirely from the field of view. No saturation pulses were employed. The volume data were reformatted through vessels of interest and also displayed as maximum intensity projections.

Gadopentetate Dimeglumine Injection

After pre-scanning, venous access was obtained via a 22 gauge angiocatheter. A dynamic acquisition was then performed during hand injection of gadopentetate dimeglumine (Berlex Laboratories, Cedar Knoll, N.J.), 0.2 millimoles/kilogram. The injection was initiated within 5 seconds of initiating the image acquisition. The injection rate was constant (within the limitations of a hand injection) and timed to last until 10–20 seconds before completion of the scan. A 5 cc normal saline chaser was given to ensure injection of the entire gadopentetate dimeglumine dose. In order to compare to the conventional, non-dynamic, gadolinium-enhanced MRA, a second, identical acquisition was then acquired without altering the imaging or prescan parameters.

Signal Measurements

Signal intensity was measured in the abdominal aorta, IVC, iliac artery and vein, renal artery and vein, celiac trunk, SMA, portal vein, hepatic vein and background tissue (including fat, skeletal muscle, kidney, liver and spleen) for 7 regions of interest per measurement. As many of these measurements as possible were obtained from the central 20 partitions and all measurements were obtained from the central 40 partitions. Identical regions of interest were used to compare vessels on the dynamic and post-gadolinium images. The standard deviation of the aorta signal was recorded as noise. Differences in the aorta and IVC signal-to-noise ratio were evaluated for each patient as well as for the means of all patients with Students t-test. In addition, the significance of differences in the mean portal vein, hepatic vein, renal vein and iliac vein signal compared to the IVC were evaluated with Students t-test. The presence of aneurysms, occlusions and stenoses (>50%) was noted on the individual dynamic images and on maximum intensity projections and compared to findings at surgery or arteriography when available.

Results

All sixteen patients tolerated the imaging and gadopentetate dimeglumine well; there were no complications. FIG. 6 illustrates the typical images obtained before, during and after injection of gadopentetate dimeglumine. Before the injection, the vessels were heavily saturated with only a few streaks of vessels visible at the edges of the 3D volume. Images obtained during injection showed enhancement of the arteries while the IVC remained indistinguishable from the background tissue. Aorta IVC signal intensity ratios, shown in TABLE 1, confirmed this preferential arterial enhancement in every patient studied. Images obtained after the injection was completed demonstrated comparable enhancement of both arteries and veins.

It should be noted that with dynamic imaging there is bright arterial as well as portal vein and splenic vein enhancement but no visible IVC or iliac vein enhancement and no in-plane saturation. Post gadopentetate dimeglumine images show comparable enhancement of both arteries and veins.

TABLE 2 provides the average signal intensity for all tissues studied for both the dynamic and post-injection sequences. With dynamic gadopentetate dimeglumine the average aorta signal-to-noise ratio was $10 \pm 0.9$ compared to $5.1 \pm 1.4$ in the IVC (p value= $<0.0001$), while post gadopentetate dimeglumine the aorta and IVC were nearly identical, $10 \pm 1.4$ and $9.5 \pm 1.3$ respectively. Although all veins were less bright than the aorta on the dynamic images compared to post gadopentetate dimeglumine images, there were variations among the veins analyzed. The iliac vein was the least enhanced, $4.7 \pm 1.6$, while the portal vein was the brightest, $8.3 \pm 1.6$ followed by the hepatic, $7.5 \pm 2.1$, and renal, $6.2 \pm 1.8$, veins; these differences were significant to the $p<0.01$ level compared to the mean IVC signal-to-noise ratio.

Angiographic and/or surgical correlation was available in 6 of the 16 patients. In the vascular segments for which definitive correlation was available, magnetic resonance arteriography correctly identified 2 occlusions (1 common iliac and 1 renal artery), 10 stenoses (4 renal artery, 2 iliac artery, 2 distal aorta, 1 inferior mesenteric artery and 1 celiac) and 6 aneurysms (3 aortic and 3 iliac artery). There was no evidence of arterial in-plane saturation in any patient. In one patient with a common iliac artery occlusion, there was no difficulty visualizing reconstituted flow distal to the occlusion.

TABLE 3 reveals an apparent trend for patients with a history of cardiac disease, claudication or aneurysms to have the greatest aorta/IVC signal intensity ratio. The sample size may have been too small to establish statistically significant correlations. Further, one patient with cardiac disease, aneurysmal disease and claudication had the highest aorta/IVC signal intensity ratio. These trends are opposite from time-of-flight imaging where cardiac disease and aneurysms are associated with image degradation.

EXAMPLE 2

In order to determine the optimal timing of contrast administration, two methods of dynamic administration, bolus and continuous infusion, were compared to non-dynamic injections and to conventional time-of-flight imaging.

Gadolinium enhanced magnetic resonance arteriography was performed in 52 patients referred for routine MRA of the abdominal aorta or branch vessels. Imaging was performed as described in Example 1. The total acquisition time was 5:08 minutes to cover approximately 36 cm of aorta and iliac artery in the superior to inferior dimension. In 20 of the patients of the dynamic gadolinium infusion imaging was performed with 28 partitions each 2 mm thick with a 256 by 256 matrix to reduce the scan time to 3:18 minutes.

After pre-scanning, venous access was obtained via a 22 gauge angiocatheter. A dynamic acquisition was then performed during hand injection of gadolinium dimeglumine (Berlex Laboratories, Cedar Knoll, N.J.) 0.2 millimoles/Kg. In 12 patients, the injection was given as a bolus. The bolus was begun within 5 seconds of starting the acquisition and completed within the first 1 to 2 minutes of the 5 minute scan. In the other 40 patients, an injection of the same dose was carefully timed to be constant and continuous over the entire period of imaging beginning within 5 seconds of commencing the acquisition and ending 20 seconds before the end of the acquisition. In all patients, a 5 cc normal saline chaser was given to ensure injection of the entire gadopentetate dimeglumine dose.

For comparison purposes, 16 of these patients were imaged with an identical acquisition after the dynamic infusion without altering the imaging or prescan parameters. Also, for comparison, axial 2D and multiple overlapping 3D (MOTSA) time-of-flight images were acquired prior to the gadolinium injection. Inferior presaturation pulses were used with the time-of-flight sequences to suppress venous in-flow.

Signal intensity was measured in all patients in the aorta, IVC and background tissues (fat and skeletal muscle) for at least 3 regions of interest per measurement for all sequences. The standard deviation of the signal within the aorta was recorded as noise.

Images obtained dynamically, during steady infusion of gadopentetate dimeglumine, showed sufficient arterial enhancement to clearly define the aorta and branch vessel anatomy while the IVC and iliac veins remained indistinguishable from the background tissues. The portal vein is visible but is not as bright as the aorta. Images obtained non-dynamically, after the injection was completed, or with a dynamic bolus injection demonstrated comparable enhancements of both arteries and veins.

Figure 7:
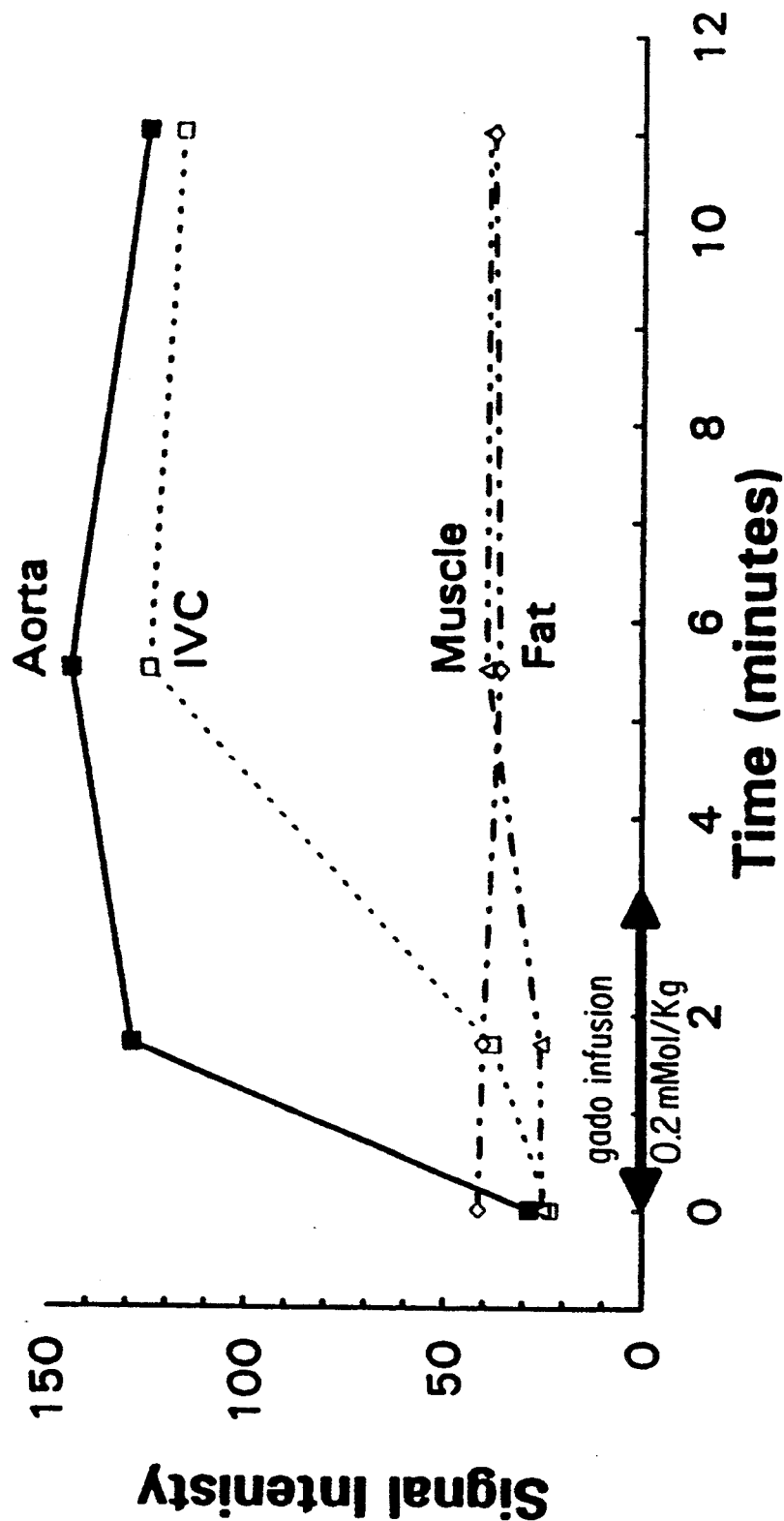
FIG. 7 illustrates region of interest analysis averaged for 3 patients who had pre-infusion, dynamic infusion, immediate post infusion and delayed 3D FT imaging. This figure shows that there is a short window, during contrast infusion, when the aorta signal intensity (solid squares) is higher than that of the IVC (open squares) and background tissues, fat (diamonds) and muscle (triangles)

The observation of significant, preferential arterial enhancement with a continuous dynamic contrast infusion was confirmed by region of interest analysis (see Table 4 and FIG. 7). The ratio of aorta to IVC signal intensity for the 5 minute infusion, $2.0 \pm 0.5$, was significantly higher than for non-dynamic imaging $1.1 \pm 0.1$ ($p<0.001$) or for the dynamic bolus $1.2 \pm 0.2$ (p $<0.001$). Even better differentiation between the aorta and IVC was obtained by injecting the same dose of gadopentetate dimeglumine more quickly over a 3:18 minute acquisition. Although this aorta-to-IVC signal intensity ratio was not as favorable as for 2D time-of-flight or MOTSA imaging, it was adequate in all cases for clearly distinguishing the aorta and abdominal aorta branch vessels from the IVC and iliac veins.

Dynamic contrast enhanced 3D imaging had no saturation, pulsatility or misregistration artifacts. Even in aneurysms, which tend to have stagnant and/or turbulent flow, there was no loss of signal. By comparison, every 2D time-of-flight study had pulsatility artifacts and some had misregistration and/or in-plane saturation artifacts. The MOTSA images had no pulsatility or misregistration artifacts but every MOTSA study showed some degree of arterial saturation and they were particularly degraded in aneurysmal segments.

Administering gadopentetate dimeglumine dynamically as a steady, continuous, infusion for the entire period of a 3D FT acquisition, at a dose of 0.2 millimoles/Kg, gives sufficient preferential arterial enhancement to visualize arteries distinctly from veins and background tissues regardless of the magnitude or direction of flow. The importance of injecting dynamically and continuously during the entire scan is illustrated by the absence of significant preferential enhancement when the contrast is administered nondynamically or as a dynamic bolus. Images obtained at a lower dose, 0.1 millimole/Kg, were not useful.

Since dynamic gadolinium enhanced MRA does not depend upon the in-flow of unsaturated spins, it eliminates some of the saturation problems that complicate routine time-of-flight imaging. The imaging volume can be oriented in any plane for optimal coverage of the vessels of interest without concern for saturation. In these patients, in-plane, coronal imaging of the aorta-iliac system reduced the image acquisition time by 5 to 20 fold over 2D time-off-light and MOTSA imaging and had superior resolution and superior aorta signal-to-noise ratios.

A 3D FT acquisition was used in this example partly because of its intrinsically high spatial resolution and high signal-to-noise and also because its main limitation, arterial saturation, is eliminated by the gadolinium. The TE was chosen to be as short as possible at a value where fat and water protons are out of phase. A short TE helps to minimize motion related phase artifacts. Having fat and water out of phase provides an element of fat suppression which improves artery-to-background contrast since fat is the brightest background tissue.

EXAMPLE 3

Figure 8A:
FIG. 8 is an illustrative example of a magnetic resonance image of a patient with an abdominal aortic aneurysm. The MRA depicts the aneurysmal aorta and aneurysmal common iliac arteries as well as severe stenoses of the right external iliac (curved arrow) and inferior mesenteric (straight arrow) arteries and a mild stenosis of the left common iliac artery. These lesions were confirmed by conventional, catheter-based arteriography (B).
Figure 8B:

MRA image data for a patient presenting with an abdominal aortic aneurysm was acquired as described in Example 1. MRA images are shown in FIG. 8.

The MRA (A) depicts the aneurysmal aorta and aneurysmal common iliac arteries as well as severe stenoses of the right external iliac (curved arrow) and inferior mesenteric (straight arrow) arteries and a mild stenosis of the left common iliac artery. The internal iliac arteries are excluded because of their posterior course. A digital subtraction angiogram (B) confirms these findings.

Various preferred embodiments of the present invention have been described. It is understood, however, that changes and modifications can be made without departing from the true scope and spirit of the present invention as defined by the following claims, which are to be interpreted in view of the foregoing.

TABLE 1

Aorta/IVC Signal Intensity Ratios for Dynamic 3D Imaging

| Patient #-sex | Age | Primary Indication | heart disease | creatinine | Signal Intensity During Injection | | | |
|---|---|---|---|---|---|---|---|---|
| | | | | | Aorta | IVC | ratio** | p value |
| 1-m | 83 | AAA | yes* | 2 | 7.9 ± 1.0 | 3.9 ± 0.6 | 2.0 | <.0001 |
| 2-f | 73 | hypertension | yes* | .8 | 11 ± 1.0 | 8.2 ± 1.3 | 1.4 | .0002 |
| 3-m | 73 | claudication | yes | 2.2 | 10 ± 2.0 | 3.7 ± 0.5 | 2.8 | .0003 |
| 4-f | 67 | hypertension | no | .9 | 10 ± 0.4 | 5.1 ± 0.6 | 2.0 | <.0001 |
| 5-f | 70 | hypertension | yes* | 3 | 8.9 ± 0.9 | 4.5 ± 0.4 | 2.0 | <.0001 |
| 6-m | 67 | renal failure | yes | 6 | 11 ± 0.5 | 4.9 ± 0.4 | 2.2 | <.0001 |
| 7-f | 80 | AAA | yes | 1.8 | 10 ± 0.4 | 5.9 ± 0.5 | 1.8 | <.0001 |
| 8-f | 76 | renal failure | yes* | 3.6 | 9.1 ± 0.6 | 5.0 ± 0.6 | 1.8 | <.0001 |
| 9-m | 68 | AAA | no | 1 | 11 ± 0.5 | 7.2 ± 0.3 | 1.4 | <.0001 |
| 10-m | 70 | claudication | yes | 1.2 | 11 ± 0.5 | 5.4 ± 0.3 | 2.0 | <.0001 |
| 11-m | 74 | hypertension | no | 1 | 8.9 ± 0.3 | 6.0 ± 0.8 | 1.5 | <.0001 |
| 12-m | 80 | hypertension | yes* | 3.2 | 10 ± 0.4 | 3.8 ± 0.9 | 2.6 | <.0001 |
| 13-m | 74 | AAA | yes | 4 | 9.8 ± 1.0 | 3.7 ± 0.8 | 2.6 | <.0001 |
| 14-f | 67 | AAA | no | 1 | 10 ± 0.3 | 5.9 ± 0.6 | 1.8 | <.0001 |
| 15-m | 67 | hypertension | no | 1.5 | 11 ± 0.9 | 4.6 ± 0.9 | 2.4 | <.0001 |
| 16-f | 71 | claudication | yes* | 6 | 11 ± 1.3 | 3.1 ± 0.6 | 3.5 | <.0001 |
| AVERAGE | | | | | 10 ± 0.9 | 5.1 ± 1.4 | 2.0 | <0.0001 |

*cardiac disease with history of CHF
**Aorta/IVC signal intensity ratio

TABLE 2

Average Signal-To-Noise Ratios During and Post Gadopentetate Dimeglumine Injection

| | Dynamic Injection | Post Injection | ratio dynamic/post |
|---|---|---|---|
| ARTERIES | | | |
| Aorta | 10 ± 0.9 | 10 ± 1.4 | 1.0 |
| Iliac Artery | 9.8 ± 1.3 | 10 ± 1.3 | .98 |
| Renal Artery | 9.7 ± 1.9 | 10 ± 2.5 | .99 |
| Celiac & SMA | 10 ± 1.7 | 11 ± 1.8 | .91 |
| VEINS | | | |
| IVC | 5.1 ± 1.4 | 9.5 ± 1.3** | .54 |
| Iliac Vein | 4.7 ± 1.6* | 9.2 ± 1.3** | .51 |
| Renal Vein | 6.2 ± 1.8* | 9.1 ± 1.9** | .68 |
| Hepatic Vein | 7.5 ± 2.1* | 8.3 ± 1.0** | .90 |
| Portal Vein | 8.3 ± 1.6* | 9.0 ± 3.3** | .92 |
| BACKGROUND | | | |
| Kidney | 7.3 ± 1.0 | 8.3 ± 1.0 | .88 |
| Liver | 5.3 ± 0.6 | 5.8 ± 1.8 | .91 |
| Spleen | 5.9 ± 2.3 | 6.3 ± 2.3 | 1.1 |
| Fat | 4.3 ± 0.7 | 4.0 ± 0.8 | 1.1 |
| Muscle | 2.4 ± 0.5 | 3.2 ± 0.7 | .75 |

*p > 0.01 compared to IVC signal intensity
**p > 0.01 compared to signal intensity for dynamic injection
***standard deviation of signal in the space outside the patient

TABLE 3

Effect of Cardiac Disease, Claudication and
Aneurysms on Aorta/IVC Signal Intensity Ratio

| Subgroup | # of Patients | Aorta/IVC* | p value |
|---|---|---|---|
| Cardiac Disease | 12 | 2.2 ± 0.6 | 0.08 |
| No Cardiac Disease | 4 | 1.8 ± 0.4 | 0.08 |
| Claudication | 4 | 2.6 ± 0.8 | 0.12 |
| No Claudication | 12 | 2.0 ± 0.4 | 0.12 |
| Aneurysm | 7 | 2.2 ± 0.7 | 0.32 |
| No Aneurysm | 9 | 2.0 ± 0.5 | 0.32 |

*Signal Intensity Ratio

TABLE 4

Effect of Injection Method on Aorta Signal-to-Noise and Contrast-to-Noise Ratios

| Pulse Sequence | Contrast Injection Method | # of patients | Image time/cm (sec/cm) | Voxel Volume (mm$^3$) | Saturation Artifacts | Pulsatility Artifacts | Aorta SNR | Aorta/IVC SI ratio | Aorta-IVC CNR | Aorta-fat CNR | Aorta muscle CNR |
|---|---|---|---|---|---|---|---|---|---|---|---|
| 2D TOF | No gado | 11 | 40 | 6.0 | yes | yes | 8.2 ± 2.8 | 3.7 ± 1 | 5.8 ± 1.9 | 5.5 ± 2 | 6.8 ± 2.4 |
| MOTSA | No gado | 12 | 92 | 4.7 | yes | no | 8.9 ± 2.5 | 2.7 ± 0.9 | 5.1 ± 1.8 | 4.9 ± 1.7 | 6.3 ± 1.9 |
| Gado: 3D | non-dynamic | 16 | 9 | 3.1 | no | no | 9 ± 2.0 | 1.1 ± 0.1 | 0.6 ± 0.5 | 5.4 ± 1.5 | 6.2 ± 1.9 |
| Gado: 3D | bolus* | 12 | 9 | 3.1 | no | no | 12 ± 2.4 | 1.2 ± 0.2 | 2.7 ± 1.4 | 7.5 ± 1.6 | 9.1 ± 1.9 |
| Gado: 3D | infusion**[1] | 20 | 9 | 3.1 | no | no | 10 ± 1.2 | 2.0 ± 0.5 | 4.7 ± 1.4 | 5.4 ± 1.1 | 7.3 ± 1.1 |
| Gado: 3D | infusion**[2] | 20 | 5.5 | 3.1 | no | no | 10 ± 2 | 2.4 ± 0.8 | 5.6 ± 1.7 | 6.8 ± 1.9 | 8.2 ± 1.7 |

SNR = signal-to-noise ratio
CNR = contrast-to-noise ratio
*gadopentetate dimeglumine given dynamically as a bolus within the first 2 minutes of the acquisition.
**gadopentetate dimeglumine given dynamically as a constant infusion spread over the entire acquisition.
[1] 5 minutes
[2] 3 minutes

What is claimed is:

1. A method of imaging an artery in a patient using magnetic resonance imaging, comprising,
   collecting image data; and
   administering a magnetic resonance contrast agent to the patient, by intravenous infusion during collection of magnetic resonance image data including data representing at least a portion of the artery and at an infusion rate including a maximum which occurs during collection of image data which corresponds to a center of k-space.

2. The method of claim 1 wherein the step of administering a magnetic resonance contrast agent includes administering the contrast agent at a variable rate during collection of image data.

3. The method of claim 2 wherein the step of administering a magnetic resonance contrast agent includes administering the contrast agent substantially throughout collection of image data.

4. The method of claim 1 wherein the magnetic resonance contrast agent is a paramagnetic contrast agent having a relaxivity.

5. The method of claim 4 wherein the infusion rate is greater than 0.0015 liters/kilogram-second$^2$ divided by the relaxivity of the paramagnetic contrast agent.

6. The method of claim 4 wherein the infusion rate is greater than 0.0025 liters/kilogram-second$^2$ divided by the relaxivity of the paramagnetic contrast agent.

7. The method of claim 4 wherein the step of administering a magnetic resonance contrast agent includes administering the contrast agent so that the concentration of the contrast agent in the artery is substantially higher than the concentration of the contrast agent in the adjacent veins during collection of image data.

8. The method of claim 7 wherein the step of administering a magnetic resonance contrast agent includes administering the contrast agent so that the concentration of the contrast agent in the arteries is sufficient to induce proton nuclear magnetic relaxation of blood with a longitudinal relaxation time (T1) of less than 270 milliseconds.

9. The method of claim 4 wherein the paramagnetic contrast agent is a gadolinium chelate.

10. The method of claim 9 wherein a dose of the gadolinium chelate is within the range of 0.05 millimoles/kilogram body weight to 0.7 millimoles/kilogram body weight.

11. The method of claim 9 wherein a dose of the gadolinium chelate is within the range of 0.15 millimoles/kilogram body weight to 0.35 millimoles/kilogram body weight.

12. The method of claim 1 wherein the step of administering a magnetic resonance contrast agent includes administering the contrast agent to allow redistribution of the contrast agent into the extravascular fluid compartment in the systemic capillary bed distal to the artery so that, during collection of the image data, the concentration of magnetic resonance contrast agent in the adjacent veins is significantly lower than the concentration of magnetic resonance contrast agent in the artery.

13. The method of claim 1 wherein the step of administering magnetic resonance contrast agent includes administering contrast agent to allow the contrast agent to be altered in the systemic capillary bed distal to the artery of interest such that the contrast agent has a lower relaxivity.

14. The method of claim 1 wherein the step of administering a magnetic resonance contrast agent includes administering the contrast agent manually through a fluid flow restrictor.

15. The method of claim 14 wherein the fluid flow restrictor is coupled to a vessel containing the magnetic resonance contrast agent and wherein the step of administering a contrast agent includes administering the contrast agent in the vessel to the patient.

16. The method of claim 1 wherein the step of administering a magnetic resonance contrast agent includes administering the contrast agent using a mechanical injector.

17. The method of claim 1 wherein the step of administering a magnetic resonance contrast agent includes administering the contrast agent using a mechanical injector which is adapted to receive a vessel containing the magnetic resonance contrast agent.

18. The method of claim 1 wherein the step of administering a magnetic resonance contrast agent includes administering the contrast agent using a mechanical injector which is coupled to a vessel containing said magnetic resonance contrast agent.

19. The method of claim 1 wherein the artery is the aorta or other peripheral artery.

20. The method of claim 1 wherein said magnetic resonance contrast agent is a paramagnetic contrast agent and the step of collecting image data includes using a 3D gradient echo pulse sequence.

21. The method of claim 1 wherein said magnetic resonance contrast agent is a paramagnetic contrast agent and TE is such that fat and water are out of phase.

22. The method of claim 1 wherein the step of collecting image data includes collecting image data representing a first image and, during the step of administering a magnetic resonance contrast agent, collecting image data representative of a second image wherein a final image is enhanced by subtracting the first image from the second image.

23. The method of claim 1 further including applying EKG gating during collection of image data to reduce cardiac motion artifacts.

24. The method of claim 1 further including applying respiratory compensation during collection of image data to reduce respiratory motion artifacts.

25. The method of claim 1 further including premedicating the patient before collection of image data to reduce the heart rate, the respiratory rate, or the cardiac output.

26. The method of claim 1 wherein the step of administering a magnetic resonance contrast agent includes administering the contrast agent in a vein remote from the artery.

27. The method of claim 1 wherein the magnetic resonance contrast agent is a paramagnetic contrast agent and $TR \leq 30$ milliseconds and flip angle is between 20° to 90°.

28. The method of claim 1 wherein the step of administering a magnetic resonance contrast agent includes administering the contrast agent using a mechanical injector which is spring-loaded, pneumatic powered, or electrically powered.

29. A method of imaging an artery in a patient using magnetic resonance imaging, comprising,
  collecting image data; and
  administering a gadolinium chelate, having a relaxivity to the patient by substantially continuous intravenous infusion throughout collection of image data including data representing at least a portion of the artery and at an infusion rate which is greater than 0.0015 liters/kilogram-second$^2$ divided by the relaxivity of the gadolinium chelate and which includes a maximum rate of infusion which temporally correlates with the collection of image data which corresponds to a center of k-space.

30. The method of claim 29 wherein the step of administering a gadolinium chelate includes administering the gadolinium chelate manually through a fluid flow restrictor.

31. The method of claim 29 wherein the step of administering a gadolinium chelate includes administering the gadolinium chelate manually through a fluid flow restrictor which is coupled to a vessel containing the gadolinium chelate.

32. The method of claim 29 wherein the step of administering a gadolinium chelate includes administering the gadolinium chelate using a mechanical injector.

33. The method of claim 29 wherein the step of administering a gadolinium chelate includes administering the gadolinium chelate using a mechanical injector which is adapted to receive a vessel containing the gadolinium chelate.

34. The method of claim 29 wherein the step of administering a gadolinium chelate includes administering the gadolinium chelate using a mechanical injector which is coupled to a vessel containing the gadolinium chelate.

35. An infusion apparatus for infusing a magnetic resonance contrast agent into a vein of a patient, during collection of image data by a magnetic resonance imaging unit, to enhance a magnetic resonance image of an artery of said patient, the infusion apparatus comprising:
  a pump, the pump adapted to receive the magnetic resonance contrast agent and adapted to administer the contrast agent to the patient, the pump includes means for controlling the rate of infusion of the magnetic resonance contrast agent into the vein, and means for matching the injection rate with the mapping of K space such that a maximum rate of infusion temporally correlates with the collection of image data which corresponds to a center of k-space.

36. The apparatus of claim 35 wherein the pump is spring-loaded, pneumatic powered, or electrically powered.

37. A method of imaging an artery in a patient using magnetic resonance imaging, comprising,
  collecting image data; and
  administering a magnetic resonance contrast agent to the patient, by intravenous infusion, substantially throughout collection of image data including data representing at least a portion of the artery and at an infusion rate having a maximum occurring during collection of image data which corresponds to a center of k-space.

38. The method of claim 37 wherein the step of administering magnetic resonance contrast agent includes administering the magnetic resonance contrast agent in a vein remote from the artery.

39. The method of claim 38 wherein the magnetic resonance contrast agent is a paramagnetic contrast agent having a relaxivity.

40. The method of claim 39 wherein the infusion rate is greater than 0.0015 liters/kilogram-second$^2$ divided by the relaxivity of the paramagnetic contrast agent.

41. The method of claim 39 wherein the infusion rate is greater than 0.0025 liters/kilogram-second$^2$ divided by the relaxivity of the paramagnetic contrast agent.

42. The method of claim 37 wherein the step of administering a magnetic resonance includes administering the contrast agent so that the concentration of the contrast agent in the artery is substantially higher than the concentration of the contrast agent in the adjacent veins.

43. The method of claim 37 wherein the step of administering a magnetic resonance contrast agent includes administering the contrast agent so that the contrast agent concentration in the arteries is sufficient to induce proton nuclear magnetic relaxation of blood with a longitudinal relaxation time (T1) of less than 270 milliseconds.

44. The method of claim 37 wherein the magnetic resonance contrast agent is a gadolinium chelate.

45. The method of claim 44 wherein the step of administering a magnetic resonance contrast agent includes administering a dose of the gadolinium chelate which is within the range of 0.05 millimoles/kilogram body weight to 0.7 millimoles/kilogram body weight.

46. The method of claim 44 wherein the step of administering a magnetic resonance contrast agent includes administering a dose of the gadolinium chelate which is within the range of 0.15 millimoles/kilogram body weight to 0.35 millimoles/kilogram body weight.

47. A method of imaging an artery in a patient using magnetic resonance imaging, comprising,
    collecting image data; and
    administering a magnetic resonance contrast agent to the patient, by intravenous infusion, during collection of image data including data representing at least a portion of the artery and at an infusion rate sufficient to provide a concentration of the contrast agent in the artery which is substantially higher than the concentration of the contrast agent in veins adjacent to the artery during collection of image data which corresponds to a center of k-space.

48. The method of claim 47 wherein the magnetic resonance contrast agent is administered substantially throughout collection of the image data.

49. The method of claim 47 wherein the magnetic resonance contrast agent is a paramagnetic contrast agent.

50. The method of claim 49 wherein the paramagnetic contrast agent is a gadolinium chelate.

51. The method of claim 50 wherein the step of administering a magnetic resonance contrast agent includes administering a dose of the gadolinium chelate which is within the range of 0.05 millimoles/kilogram body weight to 0.7 millimoles/kilogram body weight.

52. The method of claim 50 wherein the step of administering a magnetic resonance contrast agent includes administering a dose of the gadolinium chelate which is within the range of 0.15 millimoles/kilogram body weight to 0.35 millimoles/kilogram body weight.

53. The method of claim 47 wherein the magnetic resonance contrast agent is a gadolinium chelate which is administered substantially throughout collection of the image data in a vein remote from the artery.

54. The method of claim 47 wherein the step of administering a magnetic resonance contrast agent includes administering the contrast agent so that the contrast agent is capable of being altered in the systemic capillary bed distal to the artery of interest such that the contrast agent has a lower relaxivity.

55. The method of claim 47 wherein the step of administering a magnetic resonance contrast agent includes administering the contrast agent manually through a fluid flow restrictor.

56. The method of claim 47 wherein the step of administering a magnetic resonance contrast agent includes administering the contrast agent using a mechanical injector.

57. The method of claim 47 wherein the step of administering a magnetic resonance contrast agent includes administering the contrast agent using a mechanical injector which is spring-loaded, pneumatic powered, or electrically powered.

58. The method of claim 47 wherein the artery is the aorta or other peripheral artery.

59. The method of claim 47 wherein the step of collecting image data includes collecting image data representing a first image before intravenous infusion of the magnetic resonance contrast agent and, during the step of administering the magnetic resonance contrast agent, collecting image data representing a second image.

60. The method of claim 47 further including applying EKG gating during collection of image data to reduce cardiac motion artifacts.

61. The method of claim 47 further including applying respiratory compensation during collection of image data to reduce respiratory motion artifacts.

62. The method of claim 47 further including premedicating the patient before collection of image data to reduce the heart rate, the respiratory rate, or the cardiac output.

63. A method of imaging an artery in a patient using magnetic resonance imaging, comprising,
    collecting image data; and
    administering a paramagnetic contrast agent to the patient, by intravenous infusion, during collection of image data including data representing at least a portion of the artery and at an infusion rate having a maximum which temporally correlates to the collection of image data which corresponds to a center of k-space.

64. The method of claim 63 wherein the paramagnetic contrast agent is a gadolinium chelate.

65. The method of claim 64 wherein the step of collecting image data includes collecting a first image data set representing a first image and, during the step of administering a paramagnetic contrast agent, collecting a second image data set representative of a second image, and wherein the method of imaging an artery further includes generating a third image data set using the first image data set and the second image data set.

66. The method of claim 64 wherein the step of administering a paramagnetic contrast agent includes administering the contrast agent using a mechanical injector which is spring-loaded, pneumatic powered, or electrically powered.

* * * * *